US008999404B2

(12) United States Patent
Suciptan et al.

(10) Patent No.: US 8,999,404 B2
(45) Date of Patent: Apr. 7, 2015

(54) *PHALERIA MACROCARPA* EXTRACT, EXTRACTION PROCESS AND ITS USE AS CHOLESTERYL ESTER TRANSFERASE PROTEIN (CETP) INHIBITOR

(75) Inventors: Dwi Anggun Septiana Suciptan, Palembang (ID); Asep Aripin, Karawang (ID); Raymond R. Tjandrawinata, South Jakarta (ID)

(73) Assignee: Pt. Dexa Medica, Tangerang (ID)

( * ) Notice: Subject to any disclaimer, the term of this patent is extended or adjusted under 35 U.S.C. 154(b) by 19 days.

(21) Appl. No.: 14/111,939

(22) PCT Filed: Apr. 19, 2012

(86) PCT No.: PCT/IB2012/051954
§ 371 (c)(1),
(2), (4) Date: Dec. 20, 2013

(87) PCT Pub. No.: WO2012/143872
PCT Pub. Date: Oct. 26, 2012

(65) Prior Publication Data
US 2014/0099392 A1    Apr. 10, 2014

(30) Foreign Application Priority Data

Apr. 19, 2011 (ID) .............................. P00201100229

(51) Int. Cl.
*A01N 65/00* (2009.01)
*A61K 36/83* (2006.01)
*A61K 31/201* (2006.01)
*A61K 31/202* (2006.01)
*A61K 45/06* (2006.01)

(52) U.S. Cl.
CPC ............... *A61K 36/83* (2013.01); *A61K 31/201* (2013.01); *A61K 31/202* (2013.01); *A61K 45/06* (2013.01); *A61K 2236/333* (2013.01)

(58) Field of Classification Search
CPC ....................................................... A61K 36/00
USPC ......................................................... 424/725
See application file for complete search history.

(56) References Cited

U.S. PATENT DOCUMENTS

2011/0091395 A1*   4/2011   Tjandrawinata et al. ....... 424/58

* cited by examiner

*Primary Examiner* — Michael Meller
(74) *Attorney, Agent, or Firm* — Neifeld IP Law, PC

(57) ABSTRACT

An extract and/or herbal fraction and pharmaceutical preparation include extract of *Phaleria macrocarpa* which for the purpose of this invention, is referred to as DLBS1449. The herbal extract according to the teaching of this invention is effectively applicable to inhibit the expression and activity of Cholesteryl Ester Transferase Protein (CETP), increase HDL cholesterol level, decrease LDL cholesterol level without raising blood pressure therefore it is further applicable in atherosclerosis therapy.

1 Claim, 4 Drawing Sheets

*PHALERIA MACROCARPA* EXTRACT, EXTRACTION PROCESS AND ITS USE AS CHOLESTERYL ESTER TRANSFERASE PROTEIN (CETP) INHIBITOR

CROSS REFERENCE TO RELATED APPLICATIONS

This application is a national stage entry of PCT/IB2012/051954, filed Apr. 19, 2012, which published as WO 2012/143872 on Oct. 26, 2012, and claims the benefit of ID Application No. P00291100229, filed Apr. 19, 2011. The preceding applications are incorporated by reference in their entirety.

FIELD OF THE INVENTION

This invention relates to an extract of *Phaleria macrocarpa* which for the purpose of this invention, is referred to as DLBS1449, including the extraction method as well as the biological activity of the extract which shows the inhibitory activity towards Cholesteryl Ester Transferase Protein (CETP) expression and activity.

BACKGROUND OF THE INVENTION

Cholesteryl Ester Transferase Protein (CETP) is a 74-kDa glycoprotein and has hydrophobic characteristic.[1] This protein is primarily synthesized in liver and secreted to the plasma. In addition, CETP is also expressed in lower concentration in lymph, adipose tissue, heart, renal, and small intestine.[2] CETP plays a role in the Reverse Cholesterol Transport (RCT) process, where this protein mediates the exchange of cholesteryl ester in high density lipoprotein (HDL) particle for triglycerides in low density lipoprotein (LDL) and very low density lipoprotein (VLDL) particles.[1,3-5] Many prior studies had showed that CETP accelerates the cholesteryl ester accumulation process in LDL particle that leads to the inhibition of the elimination process of cholesterol from blood circulation.[4] It is reported in epidemiological studies that subjects with genetically CETP deficiency have higher amount of HDL cholesterol and lower amount of LDL cholesterol. Therefore, CETP becomes a potential therapy target in drug discovery for dyslipidemia and atherosclerosis treatment.

Nowadays, studies which emphasize at CETP are being conducted as the efforts of studying the CETP activities and its effects on the changes of HDL cholesterol and triglyceride levels in human blood plasma.[5,6] A high amount of HDL cholesterol as the result of the decrease in CETP expression is very important, whereby it has been reported that there is a negative correlation between HDL cholesterol level and the atherosclerosis risk factors.[7] The atheroprotective property of HDL is in its role in the RCT process where the excessive cholesterol in peripheral cell are distributed to the liver to be excreted.[6] There are some CETP inhibitors that have been produced and learned, such as cholesteryl ester transferase protein inhibitory peptides and CETP antisense oligodeoxynucleotides (ODNs).[8,9] However, those two inhibitors are still being studied. Besides, there was a drug as CETP inhibitor which had been developed up to clinical trial, namely torcetrapib. This product, however, did not give a positive result in the clinical trials, considering a high number of mortality in patients consuming that drug.[10] After being studied further, torcetrapib caused an increase in patients' blood pressure that led to death.

It is taught, in this present invention, the extraction process and the use of one of herbal plants, *Phaleria macrocarpa*. *Phaleria macrocarpa*, locally known as mahkota dewa, is an Indonesian native plant, usually found in yards as decorative plant or in garden as shade plant. Surprisingly, this plant, by utilizing its stems, fruit flesh, or leaves, is able to serve as CETP inhibitor. Prior to this invention, there has not been any study which explains the use or benefit of *Phaleria macrocarpa* extract as CETP inhibitor as claimed in this invention.

BRIEF DESCRIPTION OF THE INVENTION

The objects and/or solutions offered by this present invention will be set forth in the preferred embodiments. The embodiments illustrated serve the purpose of understanding the present invention, without limiting the possibilities of other embodiments in variation and/or combination and/or modification which can be learned from the practice of the present invention. The objects and/or solutions which are taught in the present invention will be realized from the elements and combination detailed in the claims herein.

To attain the solutions and in accordance with the objects of the present invention, as explained in the embodiments and broadly described in this application, the first aspect of the present invention is directed to the extract of *Phaleria macrocarpa*, which is prepared by extraction in organic solvent, that effectively serves as Cholesteryl Ester Transferase Protein (CETP) inhibitor.

The second aspect of the present invention is directed to the extract of *Phaleria macrocarpa*, or its fraction(s) or its group of compound, as a single active ingredient or in combination, in an effective amount or dose which is useful to increase the HDL cholesterol level and decrease the LDL cholesterol level.

The third aspect of the present invention is directed to a pharmaceutical composition which comprises (1) extract of *Phaleria macrocarpa*, or its fraction(s), in an effective amount or dose as a single active ingredient or in combination, and (2) carrier(s), excipient(s) or additive(s) that are pharmaceutically acceptable and physiologically suitable, which functions as, but is not limited to, CETP inhibitor.

BRIEF DESCRIPTION OF THE DRAWINGS

It will be described herewith, the description of the drawings in this patent.

DETAILED DESCRIPTION OF THE INVENTION

Figure 1:
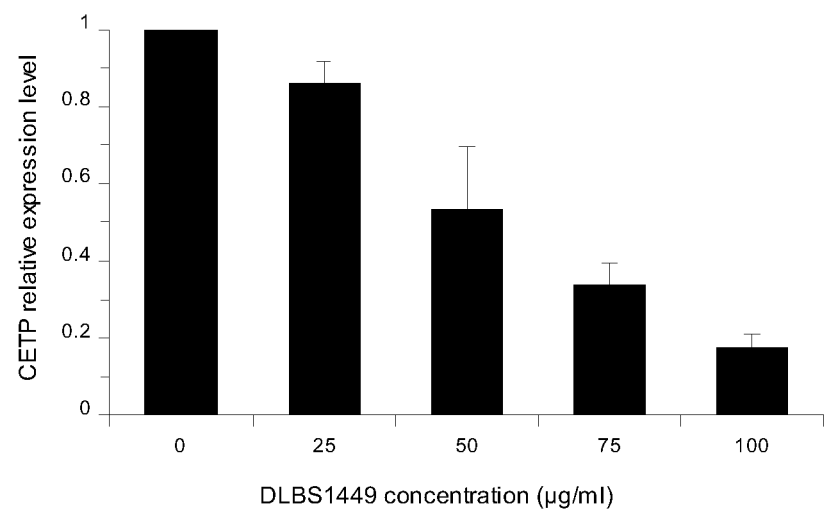
FIG. 1 is a diagram that shows the effect of DLBS1449 at 0-100 µg/ml concentration on the CETP gene expression level.

The present invention will be discussed in detail by giving examples without limiting the scope of the invention to the example provided.

Extract and/or fraction according to the teaching of the present invention is obtained from *Phaleria macrocarpa*. It will be described herewith the extraction process and the effect of DLBS1449 as CETP inhibitor.

A. Extraction Process of *Phaleria macrocarpa*

This invention teaches the extraction process of *Phaleria macrocarpa* whereby the extract having an activity as CETP inhibitor can be obtained. Extraction process which is taught in the present invention uses maceration and/or percolation system with organic solvent. Dry slices of *Phaleria macrocarpa*, preferably its fruit flesh, were extracted with organic solvent as much as 8-12 times of the weight of raw material and/or percolated in the extractor at a temperature of 10-60° C., preferably 25-50° C. The organic solvent that was used in this process included but not limited to alcohol, which included but not limited to methanol and ethanol, in absolute condition (96%) or with water as the diluent in a variety of comparison, the preferred organic solvent concentration was 70-96%. Extraction process lasted for 2-6 hours, along with stirring at 60 rpm or could be adjusted. Liquid extract was separated from the pulp by filtration. In order to obtain dry extract, liquid extract was evaporated by rotavapor at a temperature of 40-80° C. and pressure range of 70-550 mbar or could be adjusted. Furthermore, the concentrate was dried using vacuum oven for 2-4 hours to obtain dry extract. The dry extract, for the purpose of this invention is referred to as DLBS1449.

DLBS1449 which was obtained by the method as taught in this invention had been characterized further and the result showed that DLBS1449 contained, at least, the compound group(s) such as fatty acid, saponin and phenol along with other secondary metabolite or their combination that were able to serve certain biological effects. Moreover, DLBS1449 was also being identified qualitatively using Thin Layer Chromatography (TLC) method. This TLC method used silica gel plate as the stationary phase and chloroform:methanol (10:1) as the mobile phase. The TLC result showed that DLBS1449 contained the compound group(s) with Rf 0.16-0.35 that serves certain biological activity which would be described further in this patent application.

B. The Effect of DLBS1449 on CETP Expression and Activity

Cell culture used in this invention was human hepatocellular carcinoma, HepG2, wherein CETP was mostly synthesized in that liver cell. Cells were being cultured in Minimum Essential-alpha medium with addition of 10% serum, 100 μg/ml penicillin-streptomycin antibiotic, and 1 mM sodium pyruvate. Those cells were then incubated at 37° C., 5% $CO_2$ for 24 hours.

Method

In Vitro Effect of DLBS1449 on CETP Gene Expression

HepG2 cells were cultured at 6-well plate until 70% of cell density was reached. Change of medium was then performed, using serum-free medium and was then incubated for 24 hours. Those cells, then were treated with DLBS1449 in concentration of 0 (control), 25, 50, 75, and 100 μg/ml for 24 hours.

RNA Isolation and Real Time-PCR

Total RNA of HepG2 cells treated with DLBS1449 were isolated by using Trizol solution according to the procedure available from the solution. The total RNA were then measured by using NanoDrop machine and visualized by using the electrophoresis method. Moreover, RNA with good quality would be used to synthesize cDNA through RT-PCR process using PCR Thermocycler machine in certain condition that had been optimized.

Measurement of CETP Activity

This measurement was performed using CETP Inhibitor Drug Screening Kit (BioVision, USA) according to the manual available from the kit. The concentrations of DLBS1449 used were 0, 25, 50, 75, and 100 μg/ml, done in triplicate, and the same sample of DLBS1449 without CETP addition was used as control.

Result and Discussion

Figure 2:
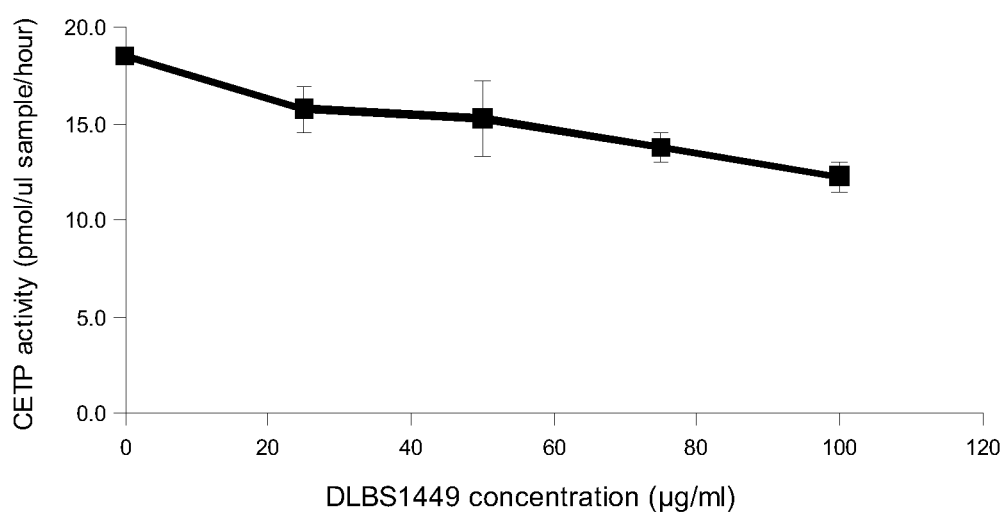
FIG. 2 is a diagram that shows the effect of DLBS1449 on the CETP activity on the protein level.

Investigation using the PCR showed that DLBS1449 is able to decrease CETP gene expression at mRNA level. The decrease of CETP gene expression is higher as the administration level of DLBS1449 increased (FIG. 1). In addition to lowering the CETP gene expression at mRNA level, DLBS1449 also has the ability as inhibitor of CETP activity at protein level, as shown in FIG. 2. This inhibition activity is in a dose-dependent manner. Prior studies claimed that CETP inhibition is one of the strategies to raise HDL cholesterol level.[5,6] The deficiency of CETP causes cholesteryl ester transfer process from HDL to VLDL and LDL cholesterol to be inhibited, therefore the formation of VLDL and LDL particle decreases and HDL level increases. This condition, wherein the amount of HDL cholesterol increases, gives anti-atherogenicity which relates to the inhibition of atheroma formation or plaque on the arterial wall.[6] Therefore, by inhibiting CETP expression and activity as taught in the present invention, DLBS1449 is believed to be able to elevate the HDL cholesterol level in blood and prevent the possibility of atherosclerosis as the LDL cholesterol level decreases. The elevation of cholesterol level was further analyzed in vivo.

C. In VIVO Effect of DLBS1449 on CETP Activity, HDL and LDL Cholesterol and Triglyceride Levels In order to ensure the effect of DLBS1449 administration on CETP activity, HDL, LDL and triglyceride levels, in vivo study was performed on male white New Zealand rabbits.

Method

The test animals were allocated into two groups, control group and treated group which were treated with DLBS1449. Rabbits in the control group were not treated with DLBS1449, otherwise rabbits in treated group were orally administered with DLBS1449 in 35 mg/1.5 kg bw dose. DLBS1449 was administered to the rabbits for 4 weeks. The measurement of CETP activity, HDL and LDL cholesterol and triglyceride levels were performed before and after the administration of extract. Samples used were plasma taken from each rabbits' ears. The measurement was performed using a specific kit for each efficacy parameter.

Result and Discussion

As shown in Table 2, the result of study showed that DLBS1449 treatment to rabbits for 4 weeks caused a decrease in CETP activity by 0.3%, while in the control group, the CETP activity increased by 5.13%. A decrease was also found for LDL cholesterol wherein the decrease in treated group was 6.8%, which was higher than that of the decrease in control group which was 3.2%. It could also be seen in Table 2 that HDL cholesterol level in the control rabbits decreased by 13.3%; on the other hand, in the treated rabbits, it increased by 15.9%. Moreover, triglyceride level in each test animals group was found to be increased, however the increase in treated group was lower than that of in the control group, 3.5% and 16.5%, respectively.

That result showed that DLBS1449 was able to effectively control the cholesterol level in the blood of rabbits where there was an increase in HDL level and a decrease in CETP activity as well as in LDL and triglyceride levels. This in vivo study result is in accordance with the in vitro study result showing that DLBS1449 is able to serve as CETP inhibitor.

TABLE 1

Characteristics and initial levels of various efficacy parameters on the test rabbits. ParametersCharacteristics and initial levels

|  | Untreated | Treated |
| --- | --- | --- |
| Number of rabbits | 6 | 6 |
| Body weights | 2.4 ± 0.52 | 2.43 ± 0.48 |
| Sex (% of male) | 100 | 100 |
| HDL cholesterol (μg/100 μl) | 0.83 ± 0.69 | 1.26 ± 0.24 |
| LDL cholesterol (μg/100 μl) | 1.56 ± 0.34 | 1.90 ± 0.85 |
| Triglycerides (nmol/100 μl) | 28.83 ± 20.16 | 48.93 ± 9.27 |
| CETP activity (pmol/μl/hour) | 133.72 ± 15.47 | 142.06 ± 6.75 |

TABLE 2

Percentage of change on initial levels of various efficacy parameters such as CETP activity, HDL and LDL cholesterols and triglyceride levels on rabbits which were treated and not treated with DLBS1449 extract.

| Parameters | (% changes on initial level) | |
| --- | --- | --- |
| HDL cholesterol (μg/100 μl) | −13.3 | 15.9 |
| LDL cholesterol (μg/100 μl) | −3.2 | −6.8 |
| Triglycerides (ng/100 μl) | 16.5 | 3.5 |
| CETP activity (pmol/μl/hour) | 5.13 | −0.3 |

D. Effect of DLBS1449 on CETP and APOA-1 on the Protein Level

HepG2 cells were cultured in flask T-75 until 70% of cell density was reached. The growth medium were then replaced with serum-free medium and incubated for 24 hours wherein the cell density had reached 80-90%. Cells were then treated with 0, 50, and 100 μg/ml of DLBS1449.

Method
Extracellular Protein Isolation

The treated mediums were collected and concentrated 10 times of the initial volume using centrifuge tube which had a membrane that was able to separate protein based on their molecular weight. In this case, membrane used was the membrane that was able to separate protein with molecular weight of more than and less than 10 kDa. The separation was performed by centrifugation at 5000 rpm for 15 minutes. Protein collected was the protein with molecular weight of more than 10 kDa. Protein concentration in the concentrated medium was then assayed using Bradford method.

CETP and ApoA-1 Protein Assay Using Western Blot Method

Isolated protein was then separated according to its molecular weight using gel containing 10% acrylamide. The SDS-PAGE electrophoresis process was performed on 100 V voltage for 150 minutes. Protein in the gel was transferred to a PVDF (Polyvinylidene Fluoride) membrane using the blotting kit operated at 500 mA for 75 minutes. After transferring process, membrane was incubated with blocking buffer (5% skimmed milk in PBS-t buffer) for 2 hours. Membrane was then incubated overnight with polyclonal antibody recognizing human ApoA-1 and CETP protein. As internal control, polyclonal antibody recognizing tubuline protein was used. Process was then continued with incubating the membrane with secondary antibody recognizing and binding to the polyclonal antibody which previously bound to ApoA-1 and CETP protein. This incubation process was conducted for 2 hours. The membrane was then given the luminol reagent. The secondary antibody would break a substrate in the luminol reagent and brought out illumination which could be detected in dark room on film paper.

Result and Discussion

The Western blot result showed that DLBS1449 was able to decrease CETP protein excreted by HepG2 cell to the medium. It can be seen in FIG. 3 wherein the CETP protein band was thinning with the increase of DLBS1449 concentration. This result was in accordance with the result in FIG. 1 which showed the decrease of CETP expression at mRNA level. The more the expression decreases, the lesser the amount of protein will be produced.

Figure 3:
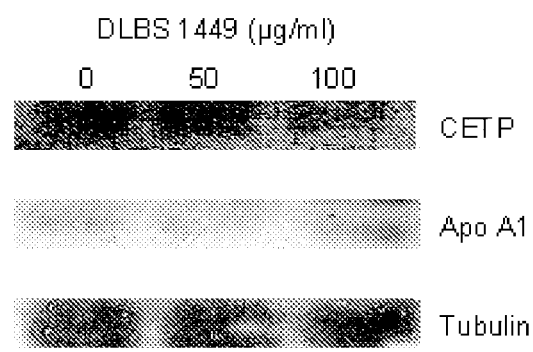
FIG. 3 is a protein band as a result of Western Blot analysis that shows the effect of DLBS1449 on CETP and ApoA-1 at the protein level.

From in vivo study result, it has been found that the level of HDL cholesterol increases after DLBS1449 treatment. Therefore, the Western Blot assay is also conducted for ApoA-1 wherein this protein is the main part of HDL particle. FIG. 3 shows that the amount of ApoA-1 protein increased, particularly at 100 μg/ml concentration. This result reveals that the increasing amount of HDL cholesterol is the result of the increase of ApoA-1 protein level synthesized by cell. HDL plasma protects against atherosclerosis by transferring the cholesterol from peripheral tissue to ester cholesteryl in liver to be excreted as bile acid. The first stage of this pathway is ApoA-1 to receive cholesterol and turn it to HDL.[11] Therefore, the increase of ApoA-1 is one of the most important factors in increasing HDL cholesterol level which plays an important role in atherosclerosis prevention.

E. Effect of OF DLBS1449 on CETP Transcription Process, Cholesterol Transportation and Blood Pressure Method This gene analysis used HepG2 cells treated with DLBS1449 in various concentrations. RNA was isolated from the HepG2 cell then analyzed using quantitative real time PCR technique where each gene expression (LXR-α, SREBP-1, SR-B1, LDL-R, ApoB, CYP11B2 dan CYP11B1) was normalized to the expression of actin gene as internal control gene. In this process, primer and annealing temperature specific for each gene were used. The result of this process was directly shown by the software in the real time PCR machine using relative expression counting method.

Figure 4:
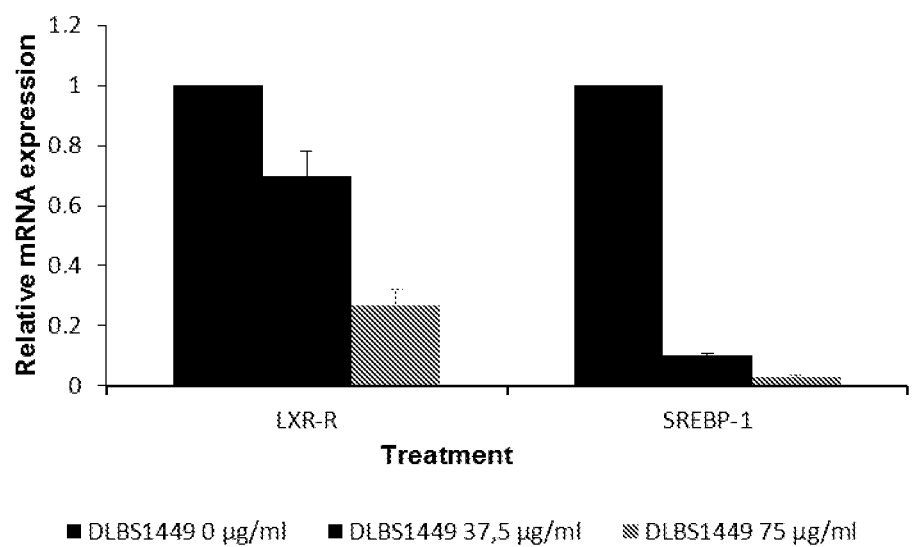
FIG. 4 is a diagram that shows the effect of the treatment of DLBS1449 on the LXR-α and SREBP-1 gene expressions that involve in the CETP transcription regulation process.

Result and Discussion
Effect of DLBS1449 on Gene Expression which Regulates CETP Transcription CETP transcription is regulated by regulator genes that affect its promoter. In this experiment, it was studied that the genes which affect that process include Liver X Receptor alpha (LXR-α) and Sterol Regulatory Element Binding Protein-1 (SREBP-1). As seen in FIG. 4, treatment of DLBS1449 decreases the expression of both genes.

LXR-α is a nuclear receptor which induces CETP transcription and keeps the Reverse Cholesterol Transport (RCT) process.[12] This gene forms heterodimer when it binds to Retinoid X Receptor (RXR) wherein that complex has an important role in regulating cholesterol levels in body. In liver, LXR-α mediates cholesterol metabolism by inducing SREBP-1 gene expression. Therefore, the decrease of LXR-α gene will also cause a decrease in SREBP-1 gene, as shown in this experiment.

SREBP-1 is a transcription factor which regulates cholesterol synthesis by activating other genes, one of them is CETP. The decrease of SREBP-1 gene expression, furthermore, indicates the decrease of CETP gene expression. That correlation expresses the negative feedback system that relates to the amount of excessive cholesterol in endoplasmic reticulum to be distributed to the liver.[11] The decrease of CETP expression previously studied is in accordance with the decrease of that CETP transcription factor expression that leads to the inhibition or decrease of the CETP gene itself in the body. This invention clearly shows that DLBS1449 controls the cholesterol levels by inhibiting CETP at its transcription level and its protein synthesis.

Effect of DLBS1449 on the Gene Expression Involved in the Cholesterol Transport Process Beside its effect on CETP, DLBS1449 is also believed to be able to affect other genes related to the cholesterol metabolism in the body. In this case, the effect of DLBS1449 on the cholesterol distribution and its effect on its constituent genes were further studied. Reverse cholesterol transport (RCT) includes the cholesterol transfer from cell to arterial wall, cholesterol distribution through blood plasma to liver as well as the excretion process through bile. This process relates to genes which facilitate that cholesterol transport.[6] Those genes include Scavenger Receptor class B type 1 (SR-B1), LDL receptor (LDL-R), apolypoprotein-B (ApoB).

Figure 5:
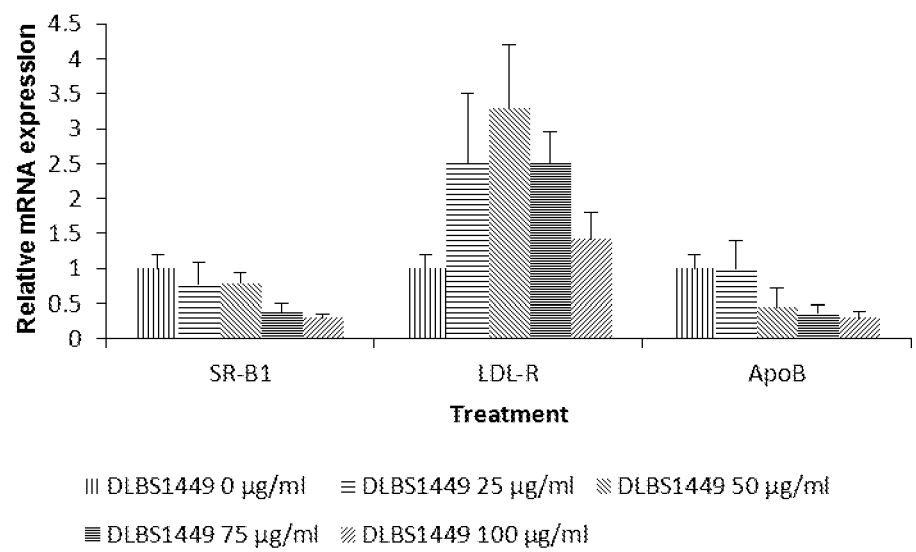
FIG. 5 is a diagram that shows the effect of the treatment of DLBS1449 on LDL-R, SR-B1, and ApoB gene expressions that involve in reverse cholesterol transport (RCT) process.

The result of the experiment showed that DLBS1449 was able to control the level of the genes which played role in cholesterol transport. It can be seen in FIG. 5 that expression of SR-B1 gene, the HDL cholesterol receptor, decreased as the dose administered increased (25-100 µg/ml), while LDL-R gene increased in its gene expression. This LDL-R gene expression had the highest increase with 50 µg/ml of DLBS1449 which was up to 3.4 times of that of control expression, while at the higher concentrations of DLBS1449, 75 and 100 µg/ml, the gene expressions were still raising, but in lower levels which were 2.6 and 1.5 times, respectively, compared to that of control (FIG. 5). Besides that, it is seen in FIG. 5 that ApoB gene expression which is the LDL cholesterol constituent, decreased as the dose administered increased (25-100 µg/ml).

Decrease in SR-B1 gene expression was inversely proportional to the HDL cholesterol levels in blood wherein the HDL metabolism decreased therefore leading to the increase of HDL cholesterol level available in the blood. SR-B1 has been known to work by mediating LDL metabolism process, but it has no role in degradation process nor serves as HDL component.[11,13] Besides, some evidence have been found showing that the decrease of CETP activity which helps RCT process is able to increase HDL metabolism selectively through SR-B1 pathway. By decreasing SR-B1 gene expression and CETP activity, the HDL cholesterol is then increased. On the other side, a condition where the LDL-R gene expression increases and ApoB gene expression decreases, showed that LDL cholesterol metabolism by liver increases through LDL receptor and there is no new LDL particle synthesis mediated by ApoB gene. Therefore, cholesterol level in blood decreases.

Effect of DLBS1449 on CYP11B2 and CYP11B1 Gene

Figure 6:
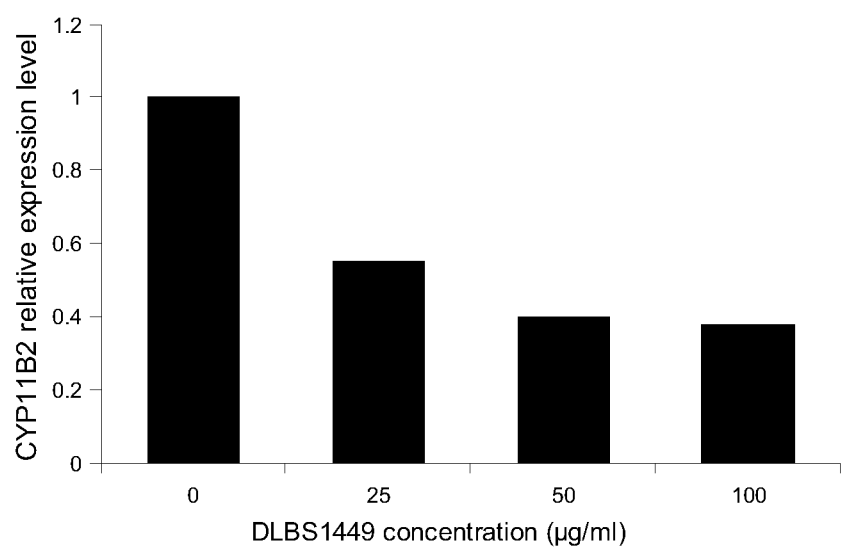
FIG. 6 is a diagram that shows the effect of DLBS1449 on the CYP11B2 gene expression.
Figure 7:
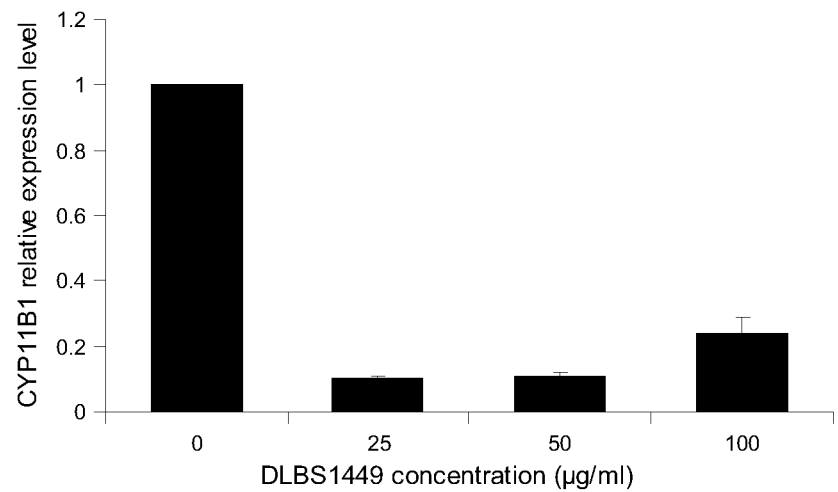
FIG. 7 is a diagram that shows the effect of DLBS1449 on the CYP11B1 gene expression.

One of CETP inhibitors which has entered clinical trial phase is torcetrapib. However, this drug could not pass the clinical trial due to the high number of mortality of patients consuming that drug. The patients' death were caused by the increase of blood pressure. Some literatures revealed that it was happened due to the increase in CYP11B2 and CYP11B1 expression, as well as the amount of aldosteron sintase associated with human blood pressure. CYP11B2 and CYP11B1 are two enzymes working at the final process of cortisol and aldosteron biosynthesis, respectively.[14] To avoid the similar event, the effect of DLBS1449 on CYP11B2 and CYP11B1 genes was then analyzed. The result of this experiment showed that DLBS1449 was able to decrease the CYP11B2 and CYP11B1 gene expressions. CYP11B2 gene expression was decreased until the dose of DLBS1449 50 µg/ml and the level of expression was seemingly constant until the dose of DLBS1449 100 µg/ml (FIG. 6) where the decrease reached 60% of the normal condition. Besides that, the decrease of gene expression was also seen in CYP11B1 gene treated up to 100 µg/ml of DLBS1449 where the decrease reached 75-80% (FIG. 7). It is concluded, therefore, that DLBS1449, in accordance with the teaching of the present invention which covers the decrease of CYP11B2 and CYP11B1 gene expressions, can be used safely as CETP inhibitor without raising blood pressure.

F. Combination Effect of Double Unsaturated Fatty Acid and DLBS1449 on CETP Gene Expression Fatty acid with various chain length and unsaturation level is known to have effect on expression of enzyme and protein in lipid metabolism. In this experiment, the effect of double unsaturated fatty acid and its combination with DLBS1449 on CETP gene expression was also studied. Double unsaturated fatty acid is known to be able to decrease the CETP gene expression. The fatty acids used in this experiment were arachidonic acid (AA) and linoleic acid (LA) wherein these types of fatty acid have high unsaturation level which are known to have significant effect on the decrease of CETP gene.

Method

HepG2 cells were cultured at 6-well plate until 60% of cell density was reached. Change of medium was then performed, using serum-free medium and incubated for 24 hours. Those cells were then treated with 4 different treatments which were 30 µM of arachidonic acid, 30 µM of linoleic acid, combination of arachidonic acid with 75 µg/ml of DLBS1449 and combination of linoleic acid with 75 µg/ml of DLBS1449. These treatments were performed for 24 hours.

RNA Isolation and Real Time-PCR

Total RNA of HepG2 cells treated with DLBS1449 were isolated using Trizol solution according to the procedure available from the solution. Total RNA were then measured using NanoDrop machine and visualized using electrophoresis method. Further, RNA with good quality will be used to synthesize cDNA through RT-PCR process using PCR Thermocycler machine in a certain condition that has been optimized.

Result and Discussion

Figure 8:
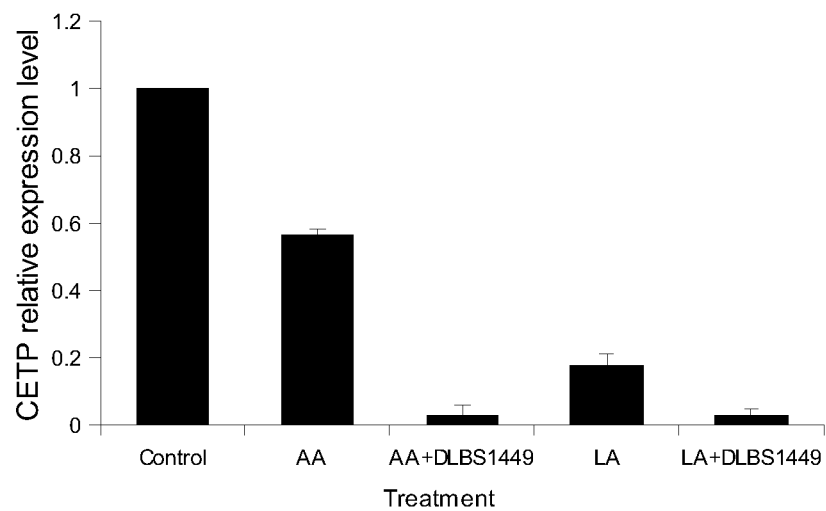
FIG. 8 is a diagram that shows the effect of arachidonic and linoleic unsaturated fatty acid, and their combination with DLBS1449 on the CETP gene expression.

At the concentration of 30 µM, these two types of double unsaturated fatty acid, arachidonic acid and linoleic acid, were able to decrease the CETP gene expression wherein the greater decrease was performed by linoleic acid (FIG. 8). When those unsaturated fatty acid were combined with 75 µg/ml of DLBS1449, the decrease of CETP gene expression were higher (FIG. 8). Concentration of fatty acid in lipoprotein particle affects the ester cholesteryl transfer mediated by CETP wherein the low concentration of fatty acid will stimulate and raise CETP activity, while on the other hand, the increase in fatty acid concentration to the optimum level will inhibit the CETP activity.[2]

Assay on mRNA level is a major determinant in CETP protein secretion process. In this experiment, it was shown that CETP expression on mRNA level was decreased by unsaturated fatty acid. The decrease in CETP expression also affects the CETP mass formed, as found in prior study.[2] Besides that, the present invention also teaches the effect of unsaturated fatty acid and DLBS1449 combination on CETP gene expression. Data showed that there was a positive correlation between double unsaturated fatty acid and DLBS1449 in decreasing CETP gene expression (FIG. 8) wherein by addition of DLBS1449, CETP gene expression performed a greater decline.

G. Compositions, Pharmaceutical Preparations, and Nutraceutical

The present invention includes pharmaceutical composition containing DLBS1449 in effective amount or dosage as active ingredient in both single and combination, including carrier materials, excipients or additives that are pharmaceutically acceptable and physiologically suitable.

In the process of preparing pharmaceutical composition as taught in the present invention, the active ingredient DLBS1449 can be mixed with, or dissolved in excipient(s), or mixed in carrier(s) that can be made in the form of capsule, sachet, paper, as well as other packaging materials.

If pharmaceutically approved excipient is used as solvent, the excipient can be in form of solid, semi-solid or liquid (oral and injection), that works as a carrier or medium for the active ingredient. Thus, pharmaceutical composition according to this invention can be produced in the form of pill, capsule, tablet, powder, sachet, solution, syrup, emulsion, suspension, effervescent tablets, gel, ointment, cream, and mouthwash, massage oil, suppository, or injection. Besides that, pharmaceutical composition containing DLBS1449 according to this invention can also be produced as supplement, vitamin, as well as food and beverage production.

Some examples of suitable excipients are microcrystalline cellulose, gelatin, lactose, dextrose, sucrose, sorbitol, mannitol, starch, calcium phosphate, calcium silicate, and others. Formulations that are appropriate with the teachings of the present invention may also contain lubricant (such as, for example, talc, magnesium stearate, mineral oil), wetting agents, preservatives, sweeteners and flavor.

Composition according to the present invention can be made with formulation that causes the active ingredient to be directly, sustained or controlled released after the patient receives such dosage forms using methods that have been applied in pharmaceutical industry. Tablet or pill according to the present invention can be coated to extend the half-life of the extract thus its frequency of use can be reduced.

Method of formulating this composition in solid form such as tablet, DLBS1449 as an active ingredient can be mixed with excipient(s) to form an initial formulation containing homogenous mixture from the composition according to the present invention. The initial formulation is a mixture containing the active ingredient of the DLBS1449 homogeneously dispersed, so it can be distributed according to the proper dosage into forms such as, for example, capsule, tablet, or pill.

Additional protection coat may be applied to the tablet or pill according to the present invention to reduce or cover the bitter taste from the composition or the active substance DLBS1449.

DLBS1449 in effective concentration or dosage according to this invention teachings is concentration or dosage where that extract serves as CETP inhibitor. Effective concentration depends on the physical condition of the patient (including body weight, age, and other factors); as well as the type, size and number of cancer cells and other targeted pathologics condition. Liquid dosage form such as beverages from herbal formulation, can be prepared by mixing the active ingredient DLBS1449 with water or other surfactant such as, for example, hydroxypropylcellulose or other compatible materials.

For preparing syrup dosage form, in herbal formulation, materials such as for producing beverages explained before are needed. However, for syrup preparation other component(s) such as thickening agent, stabilizer, and others are needed.

Semi-solid dosage form preparation such as jelly can be performed by mixing the active ingredient DLBS1449 with certain hydrocolloid such as gelatin, carrageenan, pectin, gum arabicum, guar gum, and/or other materials.

Herbal formulation in solid food preparation such as biscuit, bread and cake, can be performed by using the active ingredient DLBS1449 as a component with important effect on body health. Preparation of solid food such as biscuit, bread and cake according to the teachings of the present invention is performed as the common preparation using materials such as butter, sugar, egg, salt, and other supporting materials.

H. Industrial Application

Extract or pharmaceutical composition of DLBS1449 is able to be produced in industrial scale in production of extract, dry powder extract, and/or pharmaceutical composition, particularly for oral dosage form which can be either solid, semi-solid or liquid, or in food and beverage preparation in its use as CETP inhibitor to increase HDL cholesterol level and decrease LDL cholesterol level.

REFERENCE

1. Cho K H, Shin Y W, Choi M S, Bok S H, Jang S H, Park Y B. In vivo effects of CETP inhibitory peptides in hypercholesterolemic rabbit and cholesteryl ester transfer protein-transgenic mice. J Biochem Mol Biol. 2002; 35(2): 172-177.
2. Hirano R, Igarashi O, Kondo K, Itakura H, Matsumoto A. Regulation by long-chain fatty acids of the expression of cholesteryl ester transfer protein in HepG2 cell. Lipids. 2010; 36(4):401-6.
3. Goff W L, Guerin M, Petit L, Chapman M J, Thillet J. Regulation of human CETP gene expression: role of SP1 and SP3 transcription factors at promoter sites −690, −692, and −37. J Lipid Res. 2003; 44(7):1322-1331.
4. Klerkx A H, El Harchaoui K, van der Steeg W A, Boekholdt S M, Stroes E S, Kastelein J J, Kuivenhoven J A. Cholesterol ester transfer protein (CETP) inhibition beyond raising high-density lipoprotein cholesterol levels: Pathways by which modulation of CETP activity may alter atherogenesis. Arterioscler Thromb Vasc Biol. 2006; 26(4):706-15.
5. Barter P J, Brewer B H. Chapman M J, Hennekens, C H, Rader D J, Tall A R. Cholesterol ester transfer protein, a novel target for raising HDL and inhibiting atherosclerotic. Atherioscler Thromb Vasc Biol. 2003; 23:160-167.
6. Shah P K. Inhibition of CETP as a novel therapeutic strategy for reducing the risk of atherosclerotic disease. Eur Heart J. 2007. 28:5-12.
7. Fusegawa Y, Kelley K L, Sawyer J K, Shah R N, Rudel L L. Influence of dietary fatty acid composition on the relationship between CETP activity and plasma lipoprotein in monkeys. J Lipid Res. 2001; 42(11):1849-57.
8. Liu K, Ou J, Saku K, Jimi S, Via D P, Sparrow J T, Zhang B, Pownall H J, Smith L C, Arakawa K. Efficient nuclear delivery of antisense oligodeoxynucleotides and selective inhibition of CETP expression by Apo E peptide in a human CETP-stably transfected CHO cell line. Arterioscler Thromb Vasc Biol. 1999; 19:2207-2213.
9. Buchko G W, Rozek A, Kanda P, Kennedy M A, Cushley R J. Structural studies of a baboon (*Papio* sp.) plasma protein inhibitor of cholesteryl ester transferase. Protein Sci. 2000; 9:1548-1558.
10. Tall A R. CETP inhibitors to increase HDL cholesterol levels. N Eng J Med. 2007; 356:1364-1366.
11. Huang Z, Inazu A, Kawashiri M, Nohara A, Higashikata T, Mabuchi H. Dual effects on HDL metabolism by cholesteryl ester transfer protein inhibition in HepG2. Am J Physiol Endocrinol Metab. 2009; 284:E1210-E1219.
12. Honzumi S, Shima A, Hiroshima A, Koieyama T, Ubukata N, Terasaka N. LXRa regulates human CETP expression in vitro and in transgenic mice. Cardiovasc Prev Rehabil. 2010; 212(1):139-145.
13. Fidge N H. High density lipoprotein receptors, binding proteins and ligands. J Lipid Res. 1999; 40:187-201.
14. Hu Xiao, Dietz J D, Xia C, Knight D R, Loging W T, Smith A H, Yuan H, Perry D A, Keiser J. Torcetrapib induces aldosterone and cortisol production by an intracellar calcium-mediated mechanism independently of cholesteryl ester transfer protein inhibition. Endocrinol. 2009; 150:2211-2219.

The invention claimed is:

1. A method of treating dyslipidemia or atherosclerosis in a human in need thereof comprising administering a therapeutically effective amount of an extract of *Phaleria macrocarpa* to said human to treat the dyslipidemia or atherosclerosis in said human.

* * * * *